(12) United States Patent
Rubinstein et al.

(10) Patent No.: US 10,583,103 B2
(45) Date of Patent: Mar. 10, 2020

(54) METHOD OF TREATING HEART FAILURE WITH PRESERVED EJECTION FRACTION WITH PROBENECID

(71) Applicant: University Of Cincinnati, Cincinnati, OH (US)

(72) Inventors: Jack Rubinstein, Cincinnati, OH (US); W. Keith Jones, Fort Thomas, KY (US)

(73) Assignee: University of Cincinnati, Cincinnati, OH (US)

( * ) Notice: Subject to any disclaimer, the term of this patent is extended or adjusted under 35 U.S.C. 154(b) by 214 days.

(21) Appl. No.: 14/771,536

(22) PCT Filed: Mar. 13, 2014

(86) PCT No.: PCT/US2014/025930
§ 371 (c)(1),
(2) Date: Aug. 31, 2015

(87) PCT Pub. No.: WO2014/160153
PCT Pub. Date: Oct. 2, 2014

(65) Prior Publication Data
US 2016/0008305 A1 Jan. 14, 2016

Related U.S. Application Data

(60) Provisional application No. 61/778,826, filed on Mar. 13, 2013.

(51) Int. Cl.
| | | |
|---|---|---|
| *A61K 31/195* | (2006.01) | |
| *A61K 31/352* | (2006.01) | |
| *A61K 31/69* | (2006.01) | |
| *A61K 31/05* | (2006.01) | |
| *A61K 47/02* | (2006.01) | |
| *A61K 9/08* | (2006.01) | |
| *A61K 9/00* | (2006.01) | |
| *A61K 47/26* | (2006.01) | |

(52) U.S. Cl.
CPC .......... *A61K 31/195* (2013.01); *A61K 9/0019* (2013.01); *A61K 9/08* (2013.01); *A61K 31/05* (2013.01); *A61K 31/352* (2013.01); *A61K 31/69* (2013.01); *A61K 47/02* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,524,917 A | 8/1970 | Morgans et al. | |
| 4,952,402 A | 8/1990 | Sparks et al. | |
| 4,965,282 A | 10/1990 | Takamura et al. | |
| 4,973,600 A | 11/1990 | Takamura et al. | |
| 5,407,935 A | 4/1995 | Bigge et al. | |
| 5,444,067 A | 8/1995 | Kivlighn et al. | |
| 5,767,119 A | 6/1998 | Bigge et al. | |
| 5,942,513 A | 8/1999 | Bigge et al. | |
| 6,221,856 B1 | 4/2001 | Traynor-Kaplan et al. | |
| 7,625,696 B2 | 12/2009 | Katano | |
| 7,799,794 B2 | 9/2010 | Kivlighn et al. | |
| 7,915,012 B2 | 3/2011 | Hwang et al. | |
| 8,420,594 B2 | 4/2013 | Hulot et al. | |
| 2002/0103181 A1 | 8/2002 | Sen et al. | |
| 2003/0212123 A1 | 11/2003 | DeMello et al. | |
| 2004/0067954 A1 | 4/2004 | Eggenweiler et al. | |
| 2005/0182011 A1 | 8/2005 | Olson et al. | |
| 2006/0035840 A1 | 2/2006 | Fujikura et al. | |
| 2007/0185197 A1 | 8/2007 | Fujikura et al. | |
| 2007/0212366 A1 | 9/2007 | Greinacher et al. | |
| 2008/0051428 A1 | 2/2008 | Davis et al. | |
| 2008/0188426 A1 | 8/2008 | Fushimi et al. | |
| 2008/0207763 A1 | 8/2008 | Gulati | |
| 2009/0017015 A1 | 1/2009 | Hughes | |

(Continued)

FOREIGN PATENT DOCUMENTS

| | | |
|---|---|---|
| JP | 2009-149534 | 7/2009 |
| JP | 2009149534 | 7/2009 |

(Continued)

OTHER PUBLICATIONS

2010 Comprehensive Heart Failure Practice Guideline, Heart Failure Society of America, http://www.heartfailureguideline.org/diuretic_therapy/81.

Anjak et al., Transient Receptor Potential Vanilloid 2 (TRPV2) Stimulation Is Cardioprotective, Journal of Investigative Medicine, Apr. 23, 2010, vol. 58, No. 4, Lippincott Williams & Wilkens, US.

Arslan et al., Prognostic Value of 6-Minute Walk Test, Tex Heart Inst J 2007; vol. 34:166-169.

(Continued)

*Primary Examiner* — Shobha Kantamneni
(74) *Attorney, Agent, or Firm* — Wood Herron & Evans LLP

(57) ABSTRACT

Described herein are inventions directed to methods of treating a diastolic cardiac dysfunction and the symptoms thereof in a subject that includes administering an amount of a TRPV2 receptor agonist effective to treat the diastolic cardiac dysfunction. The TRPV2 receptor agonist may be administered in at least one of an injection, orally, or transdermally. The amount of TRPV2 receptor agonist is sufficient to result in an improved performance on quantitative diagnostic criteria. In an embodiment, the TRPV2 receptor agonist is administered over a period of about 8 hours to about 24 hours. The TRPV2 receptor agonist may be used for short term treatments, i.e., less than a week, or it may be administered in a long term manner, i.e., over a period of weeks, months, or even years. Exemplary TRPV2 receptor agonists include probenecid, 2-aminoethoxydiphenyl borate, cannabinol, cannabidiol, and combinations thereof.

12 Claims, 4 Drawing Sheets

(56) References Cited

U.S. PATENT DOCUMENTS

| | | |
|---|---|---|
| 2009/0215107 A1 | 8/2009 | Hwang et al. |
| 2010/0056464 A1 | 3/2010 | Gunic et al. |
| 2010/0160367 A1 | 6/2010 | Davis et al. |
| 2010/0290998 A1 | 11/2010 | Jones et al. |
| 2010/0292755 A1 | 11/2010 | Jones et al. |
| 2013/0046021 A1 | 2/2013 | Rubinstein et al. |

FOREIGN PATENT DOCUMENTS

| | | |
|---|---|---|
| JP | 2009-535410 | 10/2009 |
| WO | WO 2007130509 | 11/2007 |

OTHER PUBLICATIONS

Bang et al., Transient receptor potential V2 expressed in sensory neurons is activated by probenecid, Neuroscience Letters, 425 (2007) 120-125.

Bronsky et al., Diuretic Action of Benemid, Its Effect Upon The Urinary Excretion of Sodium, Chloride, Potassium and Water in Edematous Subjects, American Journal of Medicine, Feb. 18, 1955, 259-266.

Caterina, A capsaicin-receptor homologue with a high threshold for noxious heat. Nature, 1999; 398: 436-441.

Chiang et al., Dose-Dependent Kinetics of Probenecid in Rhesus Monkeys—Intravenous Bolus Studies, Pharmacology 23, 326-336, 1981.

Chiang et al., Dose-Dependent Kinetics of Probenecid in Rhesus Monkeys—Infusion Studies, Pharmacology 28: 181-187, 1984.

Damm et al., Interaction of Probenecid with Digitoxin Metabolism in Rats, Toxicology and Applied Pharmacology, Feb. 25, 1975, 246-257, vol. 33, Academic Press, Inc.

Damm et al., The Effects of Probenecid On The In Vitro Absorption of Cardiac Glycosides, European Journal of Pharmacology, Apr. 18, 1974, 157-163, vol. 28, North-Holland Publishing Company.

Database WPI, Week 200947, Thomson Scientific, London, GB, 2 pages, 2009.

Erttmann, Kinetics and Inotropic Action of Probenecid in Guinea-Pig Heart In Vitro, Experientia, Apr. 25, 1978, 1620-1621, vol. 34, issue 12, University of Hamburg, Hamburg, Germany.

Etsuko et al., Regulation of Calcium-Permeable TRPV2 Channel by Insulin in Pancreatic ?-Cells. Diabetes. Jan. 2009 vol. 58 No. 1 174-184.

Fast et al., Simultaneous Optical Mapping of Transmembrane Potential and Intracellular Calcium in Myocyte Cultures, Journal of Cardiovascular Electrophysiology, May 2000, 547-556, vol. 11, University of Alabama, Birmingham AL.

Haghighi, Superinhibition of Sarcoplasmic Reticulum Function by Phospholamban Induces Cardiac Contractile Failure Jun. 29, 2001, The Journal of Biological Chemistry, 276, 24145-24152.

Hasinoff, The Metabolites of the Cardioprotective Drug Dexrazoxane Do Not Protect Myocytes from Doxorubicin-Induced Cytotoxicity, Molecular Pharmacology, 2003, pp. 670-678, vol. 64, No. 3, The American Society for Pharmacology and Experimental Therapeutics, USA.

Iwata et al., A novel mechanism of myocyte degeneration involving the Ca21-permeable growth factor-regulated channel. (2003) Journal of Cellular Biology. 161:957-967.

Inoeu et al., Transient receptor potential Channels in cardiovascular function and disease, Circulation Research, Jul. 21, 2006, pp. 119-131.

International Preliminary Report on Patentability issued by the International Bureau of WIPO in corresponding PCT Application No. PCT/US2014/025930 dated Sep. 15, 2015, 5 pages.

International Searching Authority, International Search Report and Written Opinion in corresponding application No. PCT/US2012/060990, dated Jan. 22, 2013, 9 pages.

Jin et al. Effect of Application Volume of Ethanol-Isopropyl Myrstate Mixed Solvent System on Permeation of Zidovudine and Probenecid through Rat Skin. Drug Development and Industrial Pharmacy, 26(2), 193-198 (2000).

Kamouh et al., Contemporary Management and Research Directions in Advanced Heart Failure: Where Are We Going? Congest Heart Fail. 2011; 17: 241-7.

Koch et al., Probenecid: Novel use as a non-injurious positive inotrope acting via cardiac TRPV2 stimulation, Jul. 2012, Department of Internal Medicine, Division of Cardiovascular Diseases, University of Cincinnati, Cincinnati, Ohio, (53), 134-144.

Kramer et al., Diuretic Treatment and Diuretic Resistance in Heart Failure, American Journal of Medicine, 1999, 90-96, vol. 106, Excerpta Medica, Inc.

Medical Dictionary (online, Free Online Medical Dictionary)—definition of 'extended release' (one page).

Monet, Lysophospholipids stimulate prostate cancer cell migration via TRPV2 channel activation. Biochimica et BiophysicaActa 1793 (2009) 528-539.

Muraki et al., TRPV2 is a component of osmotic sensitive cation channels in murine aortic myocytes. Circulation Research 2003;93: 829-838.

Mylan Pharmaceuticals Inc., Morgantown, WV 26505, Mar. 2006. Probenecid tablet, film coated—(Human Prescription Drug Label) (total 4 pages).

Orengo et al., "A bichromatic fluorescent reporter for cell-based screens of alternative splicing"; Nucleic Acids Research; 34(22):e148. Epub (Nov. 16, 2006).

Packer et al., Effect of Oral Milrinone on Mortality in Severe Chronic Heart Failure. NEngl J Med 1991; 325:1468-1475.

Rajesh et al, Cannabidiol Attenuates Cardiac Dysfunction, Oxidative Stress, Fibrosis, and Inflammatory and Cell Death Signaling Pathways in Diabetic Cardiomyopathy, Journal of the American College of Cardiology, Elsevier, NY, vol. 56, Dec. 14, 2010, 2115-2125.

Robbins et al., The History and Future of Probenecid, Cardiovasc Toxicol, 2012, 1-9, vol. 12, Springer Science+Business Media, LLC.

Shibasaki et al., (2010) TRPV2 enhances axon outgrowth through its activation by membrane stretch in developing sensory and motor neurons. J Neuroscience 30:4601-12.

Tsuji et al., In Vivo Evidence for Carrier-Mediated Uptake of B-Lactam Antibiotics Through Organic Anion Transport Systems in Rat Kidney and Liver, Journal of Pharmacology and Experimental Therapeutics, Jun. 9, 1989, 315-320, vol. 253.

Vasko et al., Furosemide Absorption Altered in Decompensated Congestive Heart Failure, Annals of Internal Medicine, 1985, pp. 314-318, vol. 102, American College of Physicians.

Yang et al., Functional expression of transient receptor potential melastatin- and vanilloid-related channels in pulmonary arterial and aortic smooth muscle. American Journal of Physiology Lung Cell Molecular Physiology 2006; 290: L1267-1276.

Global status report on noncommunicable diseases 2010. Geneva, World Health Organization, 2011.

Global atlas on cardiovascular disease prevention and control. Geneva, World Health Organization, 2011.

Kochanek et al. Deaths: final data for 2009. National vital statistics reports 2011;60(3).

Burger et al. Comparison of the occurrence of ventriculary arrhtyhmias in patients with acutely decompensated congestive heart failure receiving dobutamine versus nesiritide therapy. Am J Cardiol 2001;88(1):35-39.

Singh et al. Adrenergic Regulation of Cardiac Myocyte Apoptosis. J Cell Physiol 2001;189(3):257-265.

Kunert-Keil et al. Tissue-specific expression of TRP channel genes in the mouse and its variation in three different mouse strains. BMC Genomics 2006;7:159.

Koch et al. Probenecid as a non-injurious positive inotrope in an ischemic heart disease murine model. J Cardiovas Pharm Ther 2012;18(3):280-289.

Livak and Schmittgen. Analysis of relative gene expression data using real-time quantitative PCR and the 2(-Delta Delta C(T)) Method. Methods 2001;25:402-408.

Pfaffl. A new mathematical model for relative quantification in real-time RT-PCR. Nucleic Acids Res 2001;29:e45.

Lang et al. Recommendations for chamber quantification: a report from the American Society of Echocardiography's Guidelines and

(56) References Cited

OTHER PUBLICATIONS

Standards Committee and the Chamber Quantification Writing Group, developed in conjunction with the European Association of Echocardiography, a branch of the European Society of Cardiology. Chamber Quantification Writing Group; American Society of Echocardiography's Guidelines and Standards Committee; European Association of Echocardiography. J Am Soc Echocardiogr 2005;18(12):1440-1463.

Barrio-Soria et al. Angiotensin-2-Mediated Ca2+ Signaling in the Retinal Pigment Epithelium: Role of Angiotensin-Receptor-Associated-Protein and TRPV2 Channel. PLoS ONE 2012;7(11):e49624.

Park et al. TRP vanilloid 2 knock-out mice are susceptible to perinatal lethality but display normal thermal and mechanical nociception. J Neurosci. Aug. 10, 2011;31(32):11425-36. doi: 10.1523/JNEUROSCI.1384-09.2011.

Hisanaga et al. Regulation of calcium-permeable TRPV2 channel by insulin in pancreatic beta-cells. Diabetes. Jan. 2009;58(1):174-84. doi: 10.2337/db08-0862. Epub Nov. 4, 2008.

Mihara et al. TRPV2 ion channels expressed in inhibitory motor neurons of gastric myenteric plexus contribute to gastric adaptive relaxation and gastric emptying in mice. Am J Physiol Gastrointest Liver Physiol 2013;304(3):G235-G240.

International Preliminary Report on Patentability issued by WIPO in corresponding PCT Application No. PCT/US2014/025930 dated Sep. 15, 2015 (6 pages).

Rajesh M, et al., Cannabidiol attenuates cardiac dysfunction, oxidative stress, fibrosis, inflammatory and cell death signaling pathways in diabetic cardiomyopathy, J Am Coll Cardiol. Dec. 14, 2010, 56(25):2115-2125.

O'Connell TD, Rodrigo MC, Simpson PC. Isolation and culture of adult mouse cardiac myocytes. 2007. Methods MolBiol 357:271-296.

Caterina MJ, Rosen TA, Tominaga M, Brake AJ, Julius D. A capsaicin-receptor homologue with a high threshold for noxious heat. Nature1999;398: 436-441.

Haghighi K,Superinhibition of Sarcoplasmic Reticulum Function by Phospholamban Induces Cardiac Contractile Failure Jun. 29, 2001 The Journal of Biological Chemistry, 276, 24145-24152.

Bang, S., Kim, K.Y., Too, S., Lee, S.H., Hwang, S.W. (2007) Transient receptor potential Ve expressed in sensory neurons is activated by Probenecid. Neuroscience Letters. 435: 120-125.

Beyer, R.H., Wiebelhaus, V.D., Russe, H.F., Peck, H.M. and McKinney, S.E. (1950). Benemid: An anticatabolite; its pharmacological properties. Fed. Proc. 9:258.

Boger, W.P., Pitts, F.W. and Gallagher, M.E. (1950). Benemid and Carinamide: Comparison of effect on Para-amino-salicylic acid (PAS) Plasma Concentrations. Journal of Laboratory and Clinical Medicine. 36:276-282.

Bronsky, D., Dubin, A., and Kusher, D,S. (1955). Diuretic Action of Benemid: Its effects upon the urinary excretion of sodium, chloride, potassium, and water in edematous subjects. American Journal of Medicine. 18: 259-266.

Gutman, A.B. and Yu, T.F. (1951). Benemid (p-di-n-propylsulfamyl)-benzoic acid) as uricosuric agent in chronic gouty arthritis. Trans Assoc Am Physicians. 64:279-288.

Inoue, R., Jensen, L.J., Shi, J., Morita, H., Nishida, M., Honda, A., and Ito, Y. (2006) Transient receptor potential channels in cardiovascular function and disease. Circ Res. 99:119-131.

Iwata, Y., Katanosaka, Y., Arai, Y., Komamura, K., Miyatake, K., and Shigekawa, M. (2003) A novel mechanism of myocyte degeneration involving the Ca2+-permeable growth factor-regulated channel. Journal of Cellular Biology. 161:957-967.

Shibasaki, K., Murayama, N., Ono, K., Ishizaki, Y., and Tominaga, M. (2010) TRPV2 enhances axon outgrowth through its activation by membrane stretch in developing sensory and motor neurons. J Neuroscience. 30:4601-12.

Muraki K, Iwata Y, Katanosaka Y, et al. TRPV2 is a component of osmotic sensitive cation channels in murine aortic myocytes. Circulation Research 2003;93: 829-838.

Koch SE, Gan XQ, Haar L, Jiang M, Cai WF, Robbins N, Brokamp C, Tranter M, Wang HS, Jones WK, Rubinstein J. Probenecid: A novel use as a non-injurious positive inotrope through cardiac TRPV2 stimulation. J Mol Cell Card. 2012: (53):134-144.

Robbins N, Koch SE, Tranter M, Rubinstein J. The History and Future of Probenecid. Cardiovascular Toxicology. 2011: 9145-9148.

Yang X-R, Lin M-J, McIntosh LS, and Sham JSK. Functional expression of transient receptor potential melastatin- and vanilloid-related channels in pulmonary arterial and aortic smooth muscle. American Journal of Physiology Lung Cell Molecular Physiology 2006;290: L1267-76.

Iwata Y, Katanosaka Y, Arai Y, Kamamura K, Miyatake K, Shigekawa M. A novel mechanism of myocyte degeneration involving Ca2+-permeable growth factor-regulated channel. The Journal of Cell Biology 2003;161: 957-967.

Masahiro Nagasawa1, Yuko Nakagawa1, Shigeyasu Tanaka2, Itaru Kojima1 Chemotactic peptidefMetLeuPhe induces translocation of the TRPV2 channel in macrophages. Journal of Cellular Physiology vol. 210, Issue 3, pp. 592-702, Mar. 2007.

Etsuko Hisanaga1,2, Masahiro Nagasawa1, Kohjiro Ueki1,3, Rohit N. Kulkarni4, Masatomo Mori2 and Itaru Kojima1 Regulation of Calcium-Permeable TRPV2 Channel by Insulin in Pancreatic ?-Cells. Diabetes. Jan. 2009 vol. 58 No. 1 174-184.

Kamouh A, Grancis GS. Contemporary Management and Research Directions in Advanced Heart Failure: Where Are We Going? Congest Heart Fail. 2011;17:241-7.

Packer M, Carver JR, Rodeheffer RJ, et-al. Effect of Oral Milrinone on Mortality in Severe Chronic Heart Failure. N Engl J Med 1991; 325:1468-1475.

Bishop, C. And Pfaff, W. (1955). Immediate uricosuric effect of probenecid in normal humans. ProcSocExpBiol Med. 88(3):346-348.

Boger, W.P. And Strickland, S.C. (1955). Probenecid (Benemid): Its uses and side effects in 2502 Patients. AMA Arch Intern Med. 95: 83-92.

Korf, J., and van Praag, H.M. (1970) The intravenous probenecid test: A possible aid in evaluation of the serotonin hypothesis on the pathogenesis of depressions. Psychopharmacologia. 18(1):129-32.

Wolf, D.L., Rodriguez, C.A., Mucci, M., Ingrosso, A., Duncan, B.A. and Nickens, D.J. (2003) Pharmacokinetics and renal effects of cidofovir with a reduced dose of probenecid in HIV-infected patients with cytomegalovirus retinitis. J ClinPharmacol. 43(1):43-51.

Forbes, M. and Becker, B. (1960). The transport of organic anions by the rabbit eye. II. In vivo transport of iodopyracet (Diodrast). Am J Ophthalmol. 50:867-875.

Monet MLysophospholipids stimulate prostate cancer cell migration via TRPV2channel activation. Biochimica et BiophysicaActa 1793 (2009) 528-539.

Orengo JP, Bundman D, Cooper TA.; Nucleic Acids Res. 2006;34(22):e148. Epub Nov. 16, 2006.).

Beyer, R.H., et al., "'Benemid,' p-(di-n-Propylsulfamyl)-Benzoic Acid: Its Renal Affinity and Its Elimination"; The American Journal of Physiology; vol. 166, Issue 3; pp. 625-640 (Sep. 1951).

Bishop and Pfaff., "Immediate Uricosuric Effect of Probenecid in Normal Humans"; Proc. Soc. Exp. Biol. Med. 88 (1955) 346-48.

Boger et al., "Benemid and Carinamide: Comparison of Effect on Para-Aminosalicylic Acid (PAS) Plasma Concentrations"; Journal of Laboratory and Clinical Medicine, 36; pp. 276-282 (Apr. 28, 1950).

Boger et al., "Toxicity of Carinamide", A Review of 1,997 Patients, American Journal of Medicine; pp. 35-43 (Jul. 1950).

Boger et al., "Probenecid (Benemid): Its uses and side effects in 2502 Patients"; AMA Arch Intern Med. 95(1); pp. 83-92 (1955).

Forbes, et al., "The Transport of Organic Anions by the Rabbit Eye. II. In vivo transport of iodopyracet (Diodrast)"; Am J Ophthalmol; 50. pp. 867-875 (1960).

Gutman, et al.; "Benemid (p-di-n-propylsulfamyl)-benzoic acid) as Uricosuric Agent in Chronic Gouty Arthritis"; Trans Assoc. Am Physicians; 64:279-288 (1951).

Kahn et al.; "Urate Transport in the Proximal Tubule: In vivo and in vesicle studies"; American Journal of Physiology; 249:F789-F798 (1985).

(56) References Cited

OTHER PUBLICATIONS

Koch et al., "Probenecid Increases Myocardial Contractility without Worsening Ischemic Damaga in an Infarct Model"; Abstract; The American Federation for Medical Research; p. 709 (2011).
Korf et al., "The Intravenous Probenecid Test: A Possible Aid in Evaluation of the Serotonin Hypothesis on the Pathogenesis of Depressions"; Psychopharmacologia. 18(1); pp. 129-132 (1970).
Nagasawa et al., "Chemotactic Peptide fMetLeuPhe Induces Translocation of the TRPV2 Channel in Macrophages"; Journal of Cellular Physiology, vol. 210, Issue 3, pp. 692-702, (Mar. 2007).
O'Connell et al., "Isolation and Culture of Adult Mouse Cardiac Myocytes"; Methods in Molecular Biology, vol. 357, pp. 271-296 (2007).
Wolf et al., "Pharmacokinetics and renal effects of cidofovir with a reduced dose of probenecid in HIV-infected patients with cytomegalovirus retinitis"; J ClinPharmacol. 43(1); pp. 43-51 (2003).
European Patent Application No. 14722431.5; Office Action—94(3); dated Aug. 29, 2017; 4 pages.
Bronsky, M.D., David et al.; "Diuretic Action of Benemid"; American Journal of Medicine; vol. 18, pp. 259-266 (1955).
Journal of Investigative Medicine; Midwestern Regional Program Abstracts; vol. 58, No. 4; p. 652 (Apr. 2010).
Journal of Investigative Medicine; Midwestern Regional Program Abstracts; vol. 59, No. 4; p. 709 (Apr. 2011).
Koch, Sheryl E. et al.; "Probenecid: Novel use as a non-injurious positive inotrope acting via cardiac TRPV2 stimulation"; Journal of Molecular and Cellular Cardiology; vol. 53, No. 1; pp. 134-144 (Apr. 27, 2012).
JP, Notice of Reasons for Rejection, translated and original, issued in corresponding Japanese Application No. 2015-527439, 9 pages (dated Apr. 17, 2017).

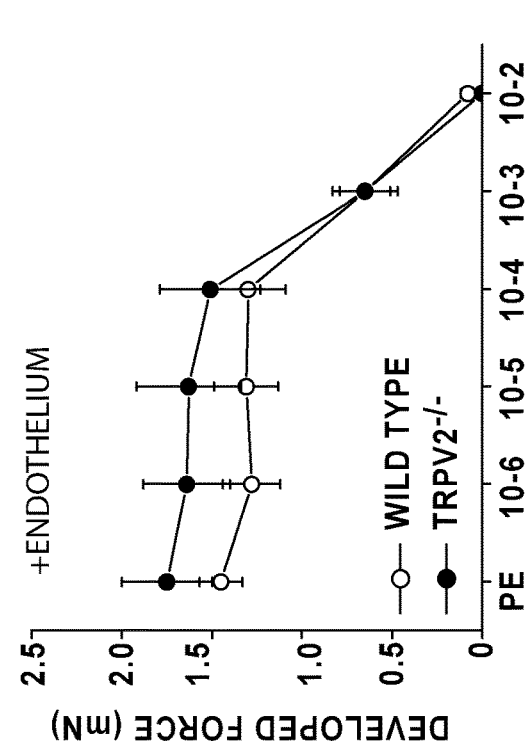
FIG. 2A
FIG. 2C
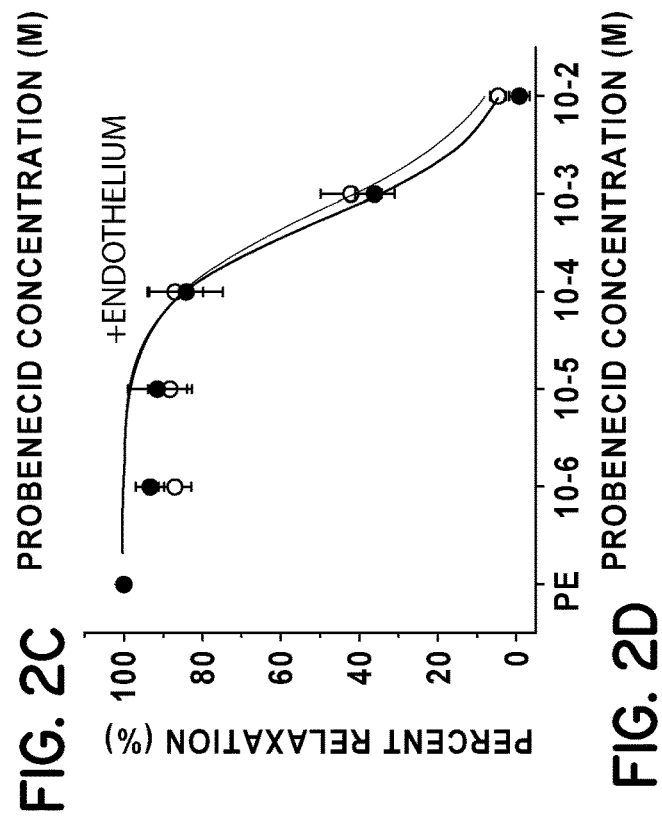
FIG. 2B
FIG. 2D
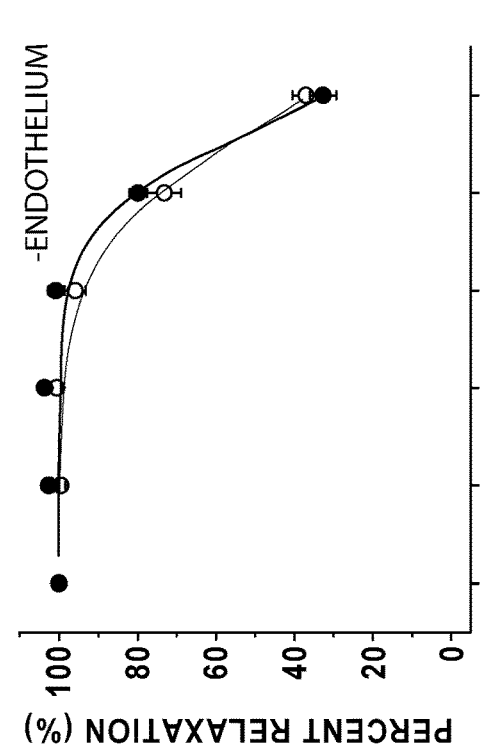

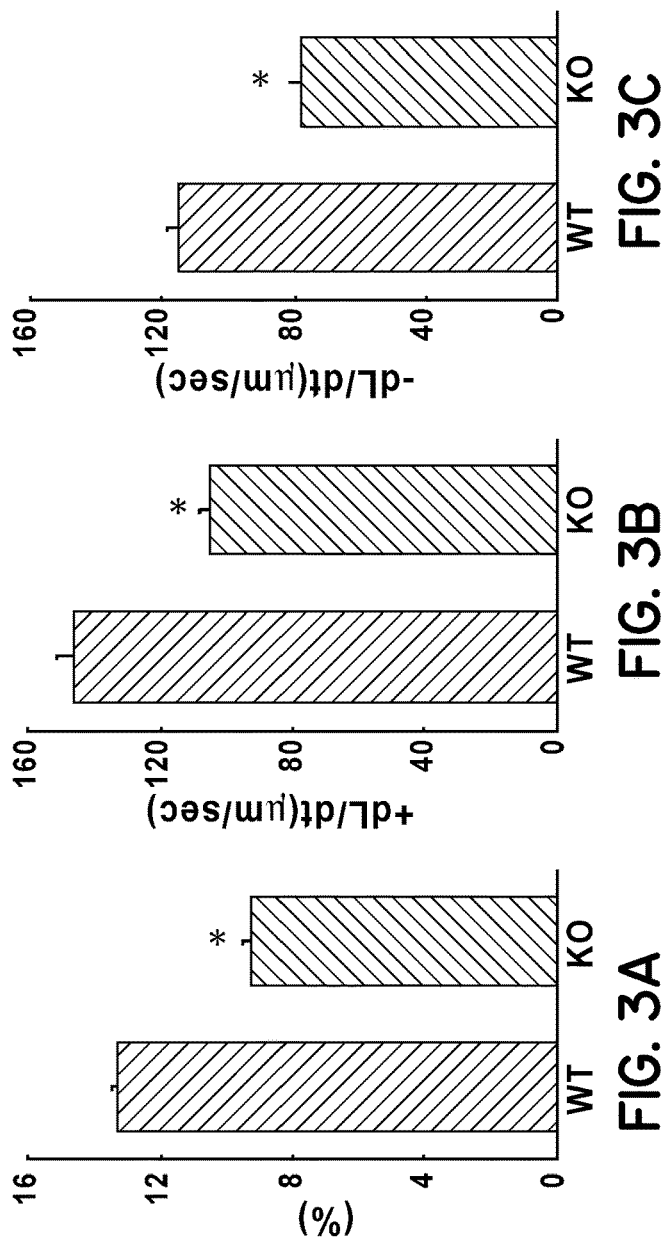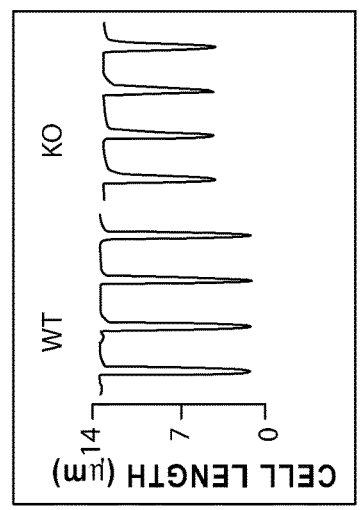

METHOD OF TREATING HEART FAILURE WITH PRESERVED EJECTION FRACTION WITH PROBENECID

RELATED APPLICATION

The Present application claims priority to U.S. Ser. No. 61/778,826 filed Mar. 13, 2013, the disclosure of which is hereby incorporated herein by reference in its entirety.

FIELD

The present invention relates generally to the treatment of a diastolic cardiac dysfunction and more particularly to the treatment of diastolic cardiac dysfunction with a TRPV2 receptor agonist.

BACKGROUND

The most common form of heart failure is a variant known as heart failure with preserved ejection fraction (HFpEF) and its precursor conditions, diastolic dysfunction, left ventricular hypertrophy with impaired left ventricular relaxation, and infiltrative cardiomyopathy with impaired left ventricular relaxation. HFpEF was previously known as "diastolic heart failure" due to the lack of capacity of the heart to expand adequately and fill during diastole, even though it is capable of contracting appropriately (i.e normal systolic function). HFpEF is almost exclusively a disorder that affects persons over 60 years of age and to this day has no known therapy. Patients suffering from HFpEF and its precursor conditions have a very poor prognosis and there is no redress of this in sight as there have been a series of negative clinical trials and very few large NIH funded studies around the country focused on this disease.

The current management of HFpEF and its precursor conditions is based on therapies known to alleviate symptoms via diuresis and reduce the workload on the heart. These therapies have been mostly tested on the other variant of heart failure (i.e., systolic heart failure, also known as HF with reduced EF) and at best only decrease the symptoms of HFpEF but do not treat the underlying cause as there are no known drug therapies that improve the diastolic function of the heart (though there are many that improve the systolic function). Options for treating patients suffering from HFpEF and its precursor conditions are needed.

The transient receptor potential (TRP) family of ion channels has been studied for many years in the nephrology and neurology literature. Several TRPs have also been found to be important mediators of vascular tone (TRPC1, TRPVc6 and TRPM4), cerebral blood flow (TRPM4), neointimal hyperplasia (TRPC1), and pulmonary hypertension (TRPC6). But until recently, only a few of the channels (such as TRPC3/6/7 in the development of cardiac hypertrophy in response to pressure overload) in this family have been found to have direct cardiac effects. With regards to the transient receptor potential vanilloid (TRPV) family, there are very interesting studies that have found a direct cardiac effect. First, it was observed that cardiac specific overexpression of TRPV2 resulted in chamber dilation of all cavities of the murine heart. Subsequently, it was observed that TRPV1 knockout mice have increased infarct size and decreased survival after ligation of the left anterior descending artery in comparison to their wild type littermates. Interestingly, others have observed that TRPV1 activation with specific agonists results in protection against ischemia/reperfusion (I/R) injury.

Probenecid has recently been identified as being a selective agonist of TRPV2. Probenecid is a highly lipid soluble benzoic acid derivative with an excellent safety profile that was developed in the 1950's to decrease the renal tubular excretion of penicillin; and has been used to increase the serum concentration of several antibiotics and antivirals since. It was also found to be a competitive inhibitor of active transport process in the brain, liver and eye and was studied in these fields but a clinical use was not established outside of its renal effects.

During the initial studies using probenecid (referred to as Benemid), probenecid was observed to have a strong uricosuric effect and quickly became the standard of treatment of gout. It was found to decrease uric acid levels in the serum via inhibition of organic acid reabsorption, such as uric acid, by the renal proximal tube by acting as a competitive inhibitor of the organic anion transporter (OAT) and thus preventing OAT-mediated reuptake of uric acid from the urine to the serum. Even though probenecid has a minimal adverse effect profile, its clinical use has declined significantly as other therapies for gout have shown improved efficacy.

SUMMARY

While the invention will be described in connection with certain embodiments, it will be understood that the invention is not limited to these embodiments. On the contrary, the invention includes all alternatives, modifications and equivalents as may be included within the spirit and scope of the present invention.

An aspect of the present invention is directed to a method of treating diastolic cardiac dysfunction including heart failure with preserved ejection fraction (HFpEF) and its precursors (e.g. diastolic dysfunction, left ventricular hypertrophy with impaired left ventricular relaxation, and infiltrative cardiomyopathy with impaired left ventricular relaxation), in a subject that includes administering an amount of a Transient Receptor Potential Vanilloid 2 ("TRPV2") agonist effective to treat the diastolic cardiac dysfunction or a symptom of the diastolic cardiac dysfunction. The TRPV agonist may be administered by at least one of an injection, an oral administration, or a transdermal administration. Preferred TRPV agonists include pharmaceutical preparations of probenecid, 2-aminoethoxydiphenyl borate (2APB), cannabinol, cannabidiol, and combinations thereof. In one embodiment of the invention, the TRPV agonist is administered in a range of about 1 mg/kg/day to about 100 mg/kg/day. When administered by injection, the TRPV agonist may be administered in at least one of a bolus injection or continuous intravenous infusion, or a bolus (loading dose) followed by intravenous infusion. In an embodiment, probenecid is administered over a period of about 8 hours to about 24 hours. Probenecid may be used for short term treatments, i.e., less than a week, or it may be administered in a long term manner, i.e., over a period of weeks, months, or even years. Probenecid may be administered in an amount sufficient to improve cardiac function clinically, resulting in an improvement in the cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof.

BRIEF DESCRIPTION OF THE DRAWINGS

The accompanying figures, which are incorporated in and constitute a part of this specification, illustrate exemplary embodiments of the invention and, together with a general description of the invention given above, and the detailed description given below, serve to explain the principles of the invention.

FIG. 2A is a graph demonstrating the dose response effect of probenecid on developed force in precontracted denuded blood vessels from wild type and TRPV2 knockout mice.

FIG. 2B is a graph demonstrating the dose response effect of probenecid on the percent relaxation in precontracted denuded blood vessels from wild type and TRPV2 knockout mice.

FIG. 2C is a graph demonstrating the dose response effect of probenecid on developed force in precontracted blood vessels from wild type and TRPV2 knockout mice.

FIG. 2D is a graph demonstrating the dose response effect of probenecid on the percent relaxation in precontracted blood vessels from wild type and TRPV2 knockout mice.

FIG. 3A is a graph depicting the percent fractional shortening in isolated cardiomyocytes from wild type and TRPV2 knockout mice.

FIG. 3B is a graph depicting the rate of contraction in isolated cardiomyocytes from wild type and TRPV2 knockout mice.

FIG. 3C is a graph depicting the rate of relaxation in isolated cardiomyocytes from wild type and TRPV2 knockout mice.

FIG. 3D is a pair of representative tracings from wild type and TRPV2 knockout mice.

DETAILED DESCRIPTION

Figure 1A:
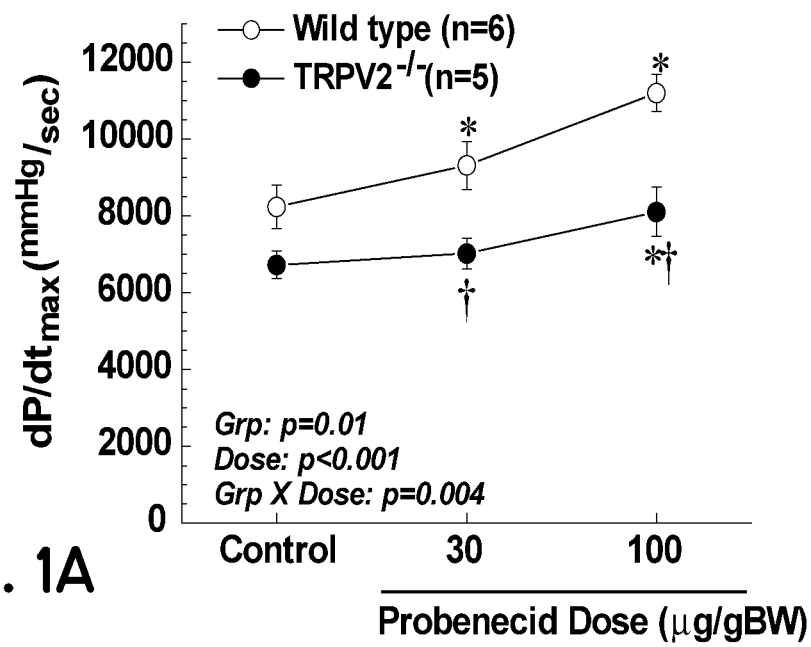
FIG. 1A is a graph depicting the baseline left ventricular contractile function in wild type and TRPV2 knockout mice.

An aspect of the invention is directed to novel methods of treating heart failure with preserved ejection fraction (HFpEF) (previously known as diastolic heart failure), and precursors of HFpEF including diastolic dysfunction, left ventricular hypertrophy with impaired left ventricular relaxation, and infiltrative cardiomyopathy with impaired left ventricular relaxation, collectively referred to herein as "diastolic cardiac dysfunction," in a subject with a TRPV2 receptor agonist. Probenecid has recently been identified as an agonist of the transient receptor potential vanilloid 2 (TRPV2) ion channel. TRPV2 is a weakly calcium-selective cation channel that is activated by swelling of cells and heat, in addition to specific agonists, like probenecid, 2-aminoethoxydiphenyl borate (2APB), cannabinol, and cannabidiol. As described herein, TRPV2 receptors located in cardiac muscle can improve cardiac relaxation. Without being held to any particular theory, agonists of TRPV2 receptors improve calcium handling in cardiac cells by improving the removal of calcium from the cytoplasm into the sarcoplasmic reticulum.

When treating diastolic cardiac dysfunction or the symptoms of diastolic cardiac dysfunction, the therapeutically effective dose of a TRPV2 receptor agonist is a dose that achieves levels of the TRPV2 receptor agonist and its active metabolites in the plasma to increase cardiac relaxation and diastolic function of the heart sufficient to alleviate at least some symptoms of cardiac dysfunction. For example, the TRPV2 receptor agonist may be administered in an amount sufficient to improve diastolic cardiac function clinically, resulting in an improvement in the diastolic cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof. The improvement can be determined, for example, based on a comparison between observations made before and after the implementation of therapy.

An aspect of the invention is directed to a method of treating diastolic cardiac dysfunction or the symptoms of diastolic cardiac dysfunction in a subject comprising administering a therapeutically effective amount of a TRPV2 receptor agonist, such as pharmaceutically acceptable formulations of probenecid, 2-aminoethoxydiphenyl borate (2APB), cannabinol, cannabidiol, and combinations thereof, to treat the symptoms of the cardiac dysfunction such as by improving the cardiac relaxation and diastolic function. The TRPV2 receptor agonist can be administered in any form that results in a plasma level of the agonist at a level sufficient to therapeutically improve cardiac relaxation and diastolic function.

An aspect of the invention is directed to a method of treating diastolic cardiac dysfunction or the symptoms of diastolic cardiac dysfunction in a subject comprising administering via injection a therapeutically effective amount of TRPV2 receptor agonist. In one embodiment, the injection is an intravenous administration. The dose required to adequately improve cardiac function by improving cardiac relaxation and diastolic function in a given patient may vary widely due to titration required by the effectiveness of treatment and the rate of clearance. Thus, in one embodiment, TRPV2 receptor agonist is administered in a range from about 1 mg/kg/day to about 100 mg/kg/day. The term day is understood to be a 24 hour cycle. In another embodiment, the extended release formulation includes a total dose of TRPV2 receptor agonist in a range from about 1 mg/kg/day to about 50 mg/kg/day. In an embodiment, the therapeutically effective amount of TRPV2 receptor agonist is in a range from about 1 mg/kg/day to about 20 mg/kg/day. In another embodiment, the therapeutically effective amount of TRPV2 receptor agonist is in a range from about 5 mg/kg/day to about 50 mg/kg/day. In another embodiment, the therapeutically effective amount of TRPV2 receptor agonist has a dosage in the range of about 10 mg/kg/day to about 100 mg/kg/day. In another embodiment, the therapeutically effective amount of TRPV2 receptor agonist has a dosage in the range of about 50 mg/kg/day to about 100 mg/kg/day.

The injection of the therapeutically effective amount of TRPV2 receptor agonist may be administered in a bolus injection, by continuous infusion, or a combination of bolus injection and continuous infusion. The term bolus injection is understood to be an injection wherein the dose is delivered over a relatively short period of time. The term continuous infusion is understood to be an injection delivered, such as with an intravenous drip, wherein the dose is delivered in a metered manner over the period of time desired for TRPV2 receptor agonist therapy. In an embodiment, the TRPV2 receptor agonist is administered via continuous infusion over a period of time ranging between about 30 min/day to about 24 hours/day. In another embodiment, therapeutically effective amount of TRPV2 receptor agonist is administered over a period of about 8 hours/day to about 24 hours/day. In some circumstances, TRPV2 receptor agonist is administered via continuous infusion on at least one day and up to on seven days. In other circumstances, TRPV2 receptor agonist may be administered for even longer periods of times, such as on days over multiple weeks, months, or even years, as necessary to treat the subject. Thus, embodiments of the invention are directed to the long term administration of TRPV2 receptor agonist to treat diastolic cardiac dysfunction and the symptoms of cardiac dysfunction.

In some instances a combination of bolus injection with continuous infusion may be desired to a treat a subject. For example, a bolus injection may be utilized to deliver a loading dose, i.e., a dose of TRPV2 receptor agonist to rapidly achieve a desired therapeutic level of TRPV2 receptor agonist in the subject, and the continuous infusion may be utilized to maintain or even titrate the desired therapeutic levels over the desired duration of treatment. For example, a subject in acute distress such as from decompensated HFpEF may require immediate treatment with a bolus intravenous injection of TRPV2 receptor agonist. After the initial bolus injection the subject may then require maintenance administration or titration of TRPV2 receptor agonist such as via continuous infusion for a period of time thereafter. In the alternative, maintenance administration of TRPV2 receptor agonist may be accomplished with subsequent bolus injections. The continuous infusion of TRPV2 receptor agonist is also useful in treating subjects with compensated HFpEF or the other forms of cardiac dysfunction.

Another aspect of the invention is directed to a method of treating the diastolic cardiac dysfunction or the symptoms of diastolic cardiac dysfunction in a subject that includes administering via oral administration of a therapeutically effective dose of TRPV2 receptor agonist to improve cardiac relaxation and diastolic function. In an embodiment, the therapeutically effective amount of TRPV2 receptor agonist is in a range from about 1 mg/kg/day to about 25 mg/kg/day. In another embodiment, the therapeutically effective amount of TRPV2 receptor agonist has a dosage in the range of about 5 mg/kg/day to about 25 mg/kg/day. In another embodiment, the therapeutically effective amount of TRPV2 receptor agonist has a dosage in the range of about 5 mg/kg/day to about 20 mg/kg/day. In another embodiment, the therapeutically effective amount of TRPV2 receptor agonist has a dosage in the range of about 5 mg/kg/day to about 15 mg/kg/day. This oral dose of TRPV2 receptor agonist may be administered in a single dose or multiple doses in a 24 hour period and may generally be administered for a period of days, weeks, months, or even years. In an embodiment, TRPV2 receptor agonist is orally administered to a subject over a period of at least two weeks, and in alternative embodiments, TRPV2 receptor agonist is administered for a plurality of months or a year or more. Thus, embodiments of the invention are directed to the long term administration of TRPV2 receptor agonist to treat diastolic cardiac dysfunction and the symptoms of diastolic cardiac dysfunction.

Another aspect of the invention is directed to a method of treating diastolic cardiac dysfunction or the symptoms of diastolic cardiac dysfunction in a subject that includes administering an extended release formulation of TRPV2 receptor agonist that maintains a therapeutic blood plasma concentration of TRPV2 receptor agonist and its active metabolites for a duration ranging between about 18 hours/day and about 24 hours/day. The extended release formulation may be an oral formulation, an injected formulation or even a transdermal formulation. In an embodiment, the extended release formulation includes a total dose of TRPV2 receptor agonist to improve diastolic cardiac function clinically, resulting in an improvement in the diastolic cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof. TRPV2 receptor agonist dosing may require titration to achieve and maintain the desired effect of improving cardiac relaxation and diastolic function. The improvement can be determined, for example, based on a comparison between observations made before and after the implementation of therapy. Thus, the dose required to adequately improve cardiac function may vary widely for a given subject as treatment progresses as well as between subjects. Thus, in one embodiment, TRPV2 receptor agonist is administered in a range from about 1 mg/kg/day to about 100 mg/kg/day. The term day is understood to be a 24 hour cycle. In another embodiment, the extended release formulation includes a total dose of TRPV2 receptor agonist in a range from about 1 mg/kg/day to about 50 mg/kg/day. In an alternative embodiment, the extended release formulation includes a total dose of TRPV2 receptor agonist in a range from about 1 mg/kg/day to about 25 mg/kg/day. In an embodiment, the therapeutically effective amount of TRPV2 receptor agonist is in a range from about 1 mg/kg/day to about 20 mg/kg/day. In another embodiment, the therapeutically effective amount of TRPV2 receptor agonist is in a range from about 5 mg/kg/day to about 50 mg/kg/day. In another embodiment, the therapeutically effective amount of TRPV2 receptor agonist has a dosage in the range of about 10 mg/kg/day to about 100 mg/kg/day. In another embodiment, the therapeutically effective amount of TRPV2 receptor agonist has a dosage in the range of about 50 mg/kg/day to about 100 mg/kg/day. In an embodiment, TRPV2 receptor agonist is orally administered to a subject over a period of at least two weeks, and in alternative embodiments, TRPV2 receptor agonist is administered for a plurality of months or a year or more. Thus, embodiments of the invention are directed to the long term administration of TRPV2 receptor agonist to treat cardiac dysfunction and the symptoms of cardiac dysfunction.

Another aspect of the invention is directed to a method of treating diastolic cardiac dysfunction or the symptoms of diastolic cardiac dysfunction in a subject comprising administering via transdermal administration, such as with a gel or patch, a therapeutically effective amount of TRPV2 receptor agonist to improve cardiac relaxation and diastolic function. In an embodiment, the transdermal formulation maintains a therapeutic blood plasma concentration of TRPV2 receptor agonist and its active metabolites for a duration ranging between about 18 hours/day and about 24 hours/day. In an embodiment, the transdermal formulation includes a total dose of TRPV2 receptor agonist to improve diastolic cardiac function clinically, resulting in an improvement in the diastolic cardiac dysfunction such as can be determined with a quantifiable clinical observations based on, for example, a standardized 6 minute walk test, improved New York Heart Association (NYHA) classification, lower diuretic dose requirement, lower serum BNP levels, normalization of serum sodium concentrations, and combinations thereof. The improvement can be determined, for example, based on a comparison between observations made before and after the implementation of therapy.

TRPV2 receptor agonist dosing may require titration to achieve and maintain the desired effect of improving cardiac relaxation and diastolic function. Thus, the dose required to adequately improve diastolic cardiac function administered transdermally may vary widely for a given subject as treatment progresses as well as between subjects. Thus, in one embodiment, TRPV2 receptor agonist is administered in a range from about 1 mg/kg/day to about 100 mg/kg/day. The term day is understood to be a 24 hour cycle. In another embodiment, the extended release formulation includes a total dose of TRPV2 receptor agonist in a range from about 1 mg/kg/day to about 50 mg/kg/day. In an alternative embodiment, the extended release formulation includes a total dose of TRPV2 receptor agonist in a range from about 1 mg/kg/day to about 25 mg/kg/day. In an embodiment, the therapeutically effective amount of TRPV2 receptor agonist is in a range from about 1 mg/kg/day to about 20 mg/kg/day. In another embodiment, the therapeutically effective amount of TRPV2 receptor agonist is in a range from about 5 mg/kg/day to about 50 mg/kg/day. In another embodiment, the therapeutically effective amount of TRPV2 receptor agonist has a dosage in the range of about 10 mg/kg/day to about 100 mg/kg/day. In another embodiment, the therapeutically effective amount of TRPV2 receptor agonist has a dosage in the range of about 50 mg/kg/day to about 100 mg/kg/day. In an embodiment, TRPV2 receptor agonist is transdermally administered to a subject over a period of at least a week, and in alternative embodiments, TRPV2 receptor agonist is administered for a plurality of months or a year or more. Thus, embodiments of the invention are directed to the long term administration of TRPV2 receptor agonist to treat diastolic cardiac dysfunction and the symptoms of diastolic cardiac dysfunction.

Achievement of a therapeutic blood plasma concentration may be evaluated by quantifying the clinical improvement in cardiac function of a subject such as with a standardized 6 minute walk test, improved New York Heart Association (NYHA) classification, lower diuretic dose requirement, lower serum BNP levels, normalization of serum sodium concentrations, and combinations thereof. The improvement and determined, for example, can be determined based on a comparison between observation made before and after implementation of therapy. For example, lowering the NYHA classification by 1, such as from 4 to 3, or increasing the distance walked in the 6 minute walk test are both indicative of quantifiable improvement. Alternatively, levels of TRPV2 receptor agonist and its metabolites may be measured in the blood of a subject. While the extended release and the transdermal formulations may be used to rescue a subject suffering from decompensated HFpEF, these formulations are particularly useful for maintenance and titration of TRPV2 receptor agonist for subjects suffering from diastolic cardiac dysfunction and the symptoms of diastolic cardiac dysfunction.

The dosing and routes of administration of TRPV2 receptor agonist may be combined to result in the optimal treatment of the subject. For example, TRPV2 receptor agonist may be administered as bolus therapy with a dose of 1/mg/kg up to 50 mg/kg in acutely ill subject with diastolic cardiac dysfunction HPpEF If this treatment is sufficient to improve symptoms then the physician may chose to initiate a continuous infusion at a rate of 1 mg/kg/hr and up to 100 mg/kg/hr with titration as needed based on each individual scenario. Furthermore, some patients may require transition to parenteral TRPV2 receptor agonist which may be administered via gel form or scored capsules with a range of 200 mg/daily and up to 4 gr/daily.

TRPV2 receptor agonist, as used herein, includes, but is not limited to, pharmaceutically acceptable forms of TRPV2 receptor agonists, such as a pharmaceutically acceptable salt or solvate. Exemplary TRPV2 receptor agonists include probenecid, Z-APB, cannabinal, and cannabidial. The preferred TRPV2 agonist is probenecid. The compositions of TRPV2 receptor agonist can be administered in vivo in a pharmaceutically acceptable carrier. By "pharmaceutically acceptable" is meant a material that is not biologically or otherwise undesirable. Thus, the compositions may be administered to a subject, without causing undesirable biological effects or interacting in a deleterious manner with any of the other components of the pharmaceutical composition in which it is contained. The carrier would naturally be selected to minimize any degradation of the TRPV2 receptor agonist and to minimize any adverse side effects in the subject, as would be known to one of skill in the art.

Suitable carriers and their formulations are described in Remington: The Science and Practice of Pharmacy (19th ed.) ed. A. R. Gennaro, Mack Publishing Company, Easton, Pa. 1995. For intravenous administration, an appropriate amount of a pharmaceutically-acceptable salt is used in the formulation to render the formulation isotonic. Examples of the pharmaceutically-acceptable carriers include, but are not limited to, saline, Ringer's solution and dextrose solution. The pH of the solution is in a pharmaceutically acceptable range, preferably from about 5 to about 8.5, and more preferably from about 7.8 to about 8.2. Further carriers include sustained release preparations such as semipermeable matrices of solid hydrophobic polymers containing the pharmaceutical composition, which matrices are in the form of shaped articles, e.g., films, liposomes or microparticles. It will be apparent to those persons skilled in the art that certain carriers may be more preferable depending upon, for instance, the route of administration and concentration of composition being administered. For example, persons skilled in the art may choose a particular carrier suitable for introduction to the body by injection, as described above, or ingestion.

In one embodiment, an injectable formulation of TRPV2 receptor agonist is prepared by dissolving the TRPV2 receptor agonist powder (acid form), such as probenecid, in 0.1 molar sodium hydroxide. This solution is then diluted with 0.2M phosphate buffer (pH=7.4). The TRPV2 receptor agonist is then diluted with saline or other carrier suitable for intravenous injection to a stock concentration, such as about 4.2 mg/ml for probenacid, to form a stock solution. The stock solution may then be diluted in saline or other injectable solution to the desired dose for administration.

For ingestion, TRPV2 receptor agonist may be formed into a tablet, capsulized, or dissolved or suspended in a liquid or gel as known to those of ordinary skill in the art for oral administration of a drug. In some embodiments, TRPV2 receptor agonist is formulated for sustained release, such as with the use of one or more excipients that control the release of TRPV2 receptor agonist over a specified period of time for absorption by the subject.

The pharmaceutical compositions of TRPV2 receptor agonist may also include binders, thickeners, diluents, buffers, preservatives, surface active agents, and the like in addition to the TRPV2 receptor agonist and carriers.

The disclosed compositions may be suitable for systemic administration. For example the compositions may be administered by other means known in the art, such as orally, parenterally (e.g., intravenous injection, intramuscular injection, intraperitoneal injection, or subcutaneous injection), suppository, or even transdermally such as through a gel or patch formulation. Such formulations may be prepared as described above or as is known to those of ordinary skill in the art.

EXAMPLE

The role of TRPV2 in cardiac relaxation was evaluated in rodents using the TRPV2 receptor agonist, probenecid.

Probenecid resulted in improved cardiac relaxation and improved diastolic function suggesting that TRPV2 receptor agonists may be useful in the treatment of diastolic cardiac dysfunctions such HfpEF and its precursor conditions.

Methods

Animals.

All animal procedures were performed with the approval of the Institutional Animal Care and Use Committee (IACUC) of the University of Cincinnati and in accordance with the *Guide for the Care and Use of Laboratory Animals* (NIH, revised 1996). All wild type (WT) mice (B6129SF2/J F2 and C57BL6J, Jackson laboratories) and TRPV2$^{-/-}$ mice (breeding pairs provided by Dr. M. Caterina, John's Hopkins, Baltimore, Md.) were males at 12-16 weeks of age (REF). Prior to experiments, mice were maintained on normal rodent chow and water ad libitum, and on a 14 hr/10 hr light/dark cycle (6 AM to 8 PM).

Solutions and Doses.

Water soluble probenecid (Molecular Probes, Life Technologies, Eugene, Oreg.) was used for all of the myocyte experiments.

Echocardiography.

All echocardiographic studies were performed with a Vevo 2100 Ultrasound system (Visualsonics, Toronto CA) with an MS400 probe (30 MHz centerline frequency) and were post-processed at a separate workstation with Vevostrain software (Visualsonic, Vevo2100, v1.1.1 B1455). Images were obtained from a parasternal long axis (PSLAX) and short axis (SAX) views at between 2 and 10 mm in depth in both M-mode and B-mode. From the M-mode images, left ventricular cavity size and wall thickness was measured and the ejection fraction (EF), fractional shortening (FS), stroke volume (SV) and cardiac output (CO) calculations were obtained as previously described (REF). Mice were anesthetized with inhaled isoflurane (1.5-2%).

Cardiovascular Function In Vivo.

Measurements of left ventricular performance and regional blood flow were performed in separate groups of WT and TRPV2$^{-/-}$ mice as previously described {Lorenz, 2008#1}. Briefly, mice were anesthetized with an intraperitoneal injection of ketamine (50 μg/gBW) and inactin (thiobutabarbital, 100 μg/gBW, Sigma, MA). A tracheotomy was performed (PE-90), and body temperature was monitored and maintained with a feedback-controlled heating table. The right femoral artery was cannulated with fluid-filled polyethylene tubing for measurement of blood pressure and connected to a low compliance pressure transducer (COBE Cardiovascular, Arvada, Colo.). The right femoral vein was cannulated for delivery of drugs. A high fidelity, 1.2F Scisense pressure catheter (Scisense, London, ON, Canada) was inserted into the right carotid artery and advanced into the left ventricle to monitor cardiac performance. ECG leads were placed on the right and left arms, and left leg and connected to a BIOAmp (ADInstruments, Colorado Springs, Colo.). For carotid blood flow measurements, the left carotid artery was isolated and fitted with a 0.5-PSB perivascular flow probe connected to a TS420 flow meter (Transonic Systems, Ithaca, N.Y.). Pressure, flow, and ECG signals were recorded and analyzed using a PowerLab system (ADInstruments). Hemodynamic measurements were taken at the basal state and after the administration of 30 and 100 μg/g doses of probenecid i.v., with 5 minutes between each dose (100 μg/μl delivered as 0.3 and 1.0 μl/gBW bolus). Measurements were taken from the final 30-40 seconds of each dosage period. Maximum dP/dt (dP/dt$_{max}$) and dP/dt at 40 mmHg of developed pressure (dP/dt$_{40}$) were calculated from the first derivative of the pressure waveforms. Cerebral vascular resistance (CVR) was calculated from recorded channels of mean arterial pressure and mean cerebral blood flow (CVR=MAP/CBF).

Isolated Cardiomyocytes.

Cardiac myocytes were isolated according to routine techniques. Briefly, adult mice were anesthetized with sodium pentobarbital (50 mg/kg); hearts were excised and perfused on a Langendorff apparatus with oxygenated solution containing 0.65 units/ml Liberase TH (Roche, Indianapolis, Ind.), at 37° C. Following digestion the left ventricular tissue was excised, minced, pipette-dissociated, and filtered through a 240-μm screen. The cell suspension was then sequentially washed in 25, 100, 200 μm and 1 mM Ca-Tyrode and resuspended in 1.8 mM Ca-Tyrode for further analysis. All experiments were carried out at room temperature (22-25° C.) in standard Tyrode solution containing (mM): 140 NaCl, 5 KCl, 1 MgCl2, 10 glucose, 10 HEPES, 1.8 CaCl2 and pH 7.4 adjusted with NaOH.

Cell Shortening and Intracellular Calcium Measurements ([Ca] i).

Cells were paced with a stimulation frequency of 0.5 Hz using a pair of platinum electrodes that delivered voltage pulses generated by a Grass stimulator (model S88, Grass, West Warwick, R.I., USA). Cell contractions were measured using a video edge detector (Crescent Electronics model VED-105, UT, USA) and the signal was digitized and recorded on a computer. For Ca$^{2+}$ signal measurements, cells were loaded with the membrane-permeable form of the fluorescent Ca$^{2+}$ indicator Fura-2 (Fura-2/AM; 2 μM) and alternately excited at 340 and 380 nm by a Delta Scan dual-beam spectrophotofluorometer (Photon Technology International) at baseline conditions and upon rapid application of 10 mM caffeine. Ca$^{2+}$-transients were expressed as the 340/380 nm ratio of the resulting 510 nm emissions. SR Ca$^{2+}$ load was measured upon rapid application of 10 mM caffeine. Data were analyzed by Felix software (Photon Technology International).

Vascular Smooth Muscle Reactivity in Isolated Aorta.

Analyses of contractile properties of vascular smooth muscle were performed in both intact (+E) and endothelium-denuded (−E) thoracic aortae using a DMT myograph (Danish Myo technology, Marietta Ga.). Aortae were dissected and in some, the endothelium removed mechanically by gently rubbing the endothelial surface with a 30 gauge needle. Rings were mounted on DMT Multi-Wire Myograph System using 190 μm stainless steel pins. The bath solution contained (in mmol/L) NaCl 118, KCl 4.73, MgCl$_2$ 1.2, EDTA 0.026, KH$_2$PO$_4$ 1.2, CaCl$_2$ 2.5, and glucose 5.5, buffered with 25 NaH$_2$CO$_3$; pH, when bubbled with 95% O$_2$/5% CO$_2$, was 7.4 at 37° C. Data were collected and analyzed using a PowerLab system (ADInstruments). Resting length of each aorta was set to 90% of the estimated circumference at an estimated transmural pressure of 100 mmHg using the AD Instruments DMT normalization module. Before the start of the experiment, each aortic segment was challenged with 100 mMKCl and 10 μM phenylephrine to ensure reproducible forces. Cumulative concentration-force relationships for increasing doses of probenecid, from $10^{-7}$ M to $10^{-2}$ M, were first tested in order to examine whether probenecid can induce contraction. In separate experiments to examine the relaxing effects of probenecid, vessel rings were first contracted with 3 μM phenylephrine, and then exposed to increasing concentrations of probenecid from $10^{-7}$ M to $10^{-2}$. Maximal force of contraction for 3 μM phenylephrine and the EC$_{50}$ for the relaxing effects of probenecid were determined using a logistic non-linear curve-fitting routine (OriginLab, Northampton Mass.).

Data Analysis.

Statistical analysis was performed by analysis of variance (ANOVA) using either a single factor within-subjects design, or a two- or three-factor mixed design with repeated measures as appropriate. Individual contrasts were used to compare group effects and interactions when needed, and the Tukey post-hoc test was used to compare individual means where appropriate (SigmaStat v3.5, Point Richmond, Calif.). Data are presented as means±S.E.M., and differences were regarded as significant at P<0.05.

Results

In vivo response to probenecid in wild type and TRPV2$^{-/-}$ mice.

Invasive Cardiac Hemodynamics.

Figure 1B:
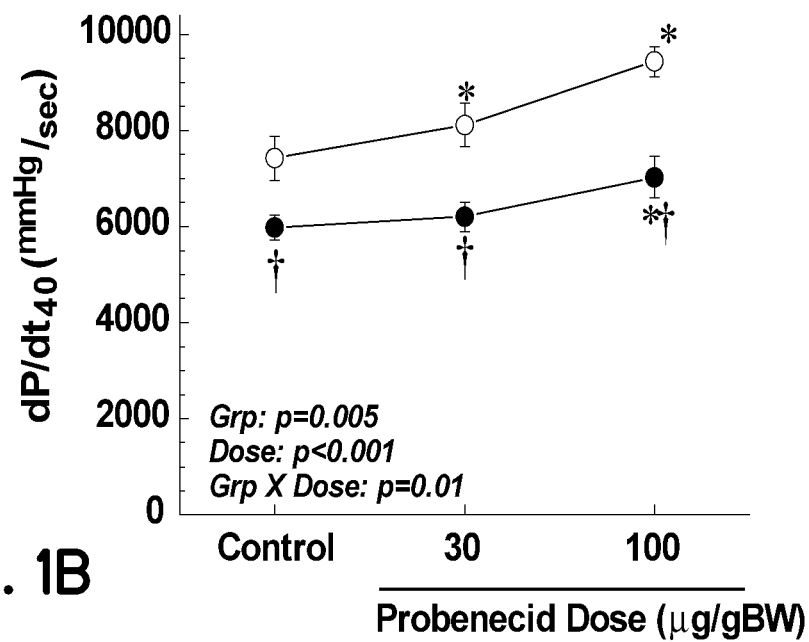
FIG. 1B is a graph depicting the baseline left ventricular contractile function in wild type and TRPV2 knockout mice.
Figure 1C:
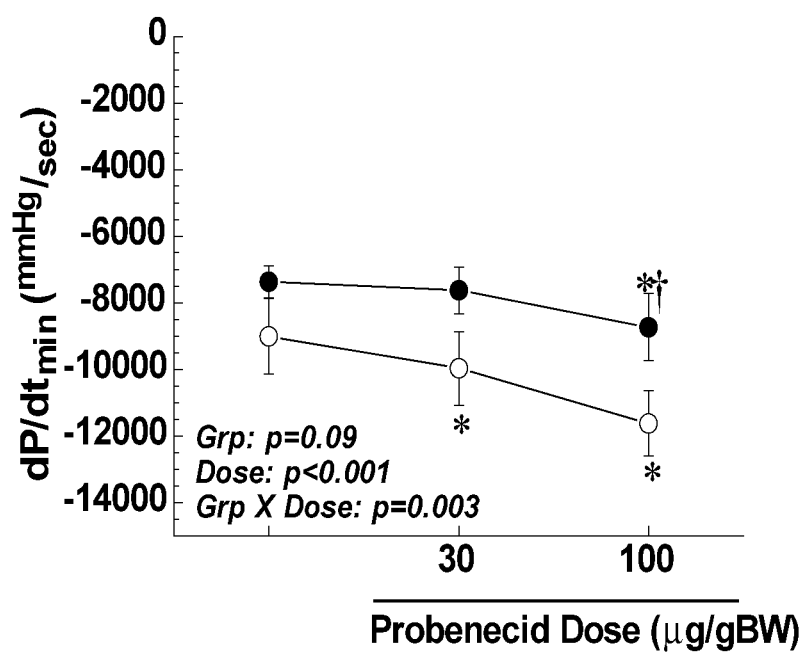
FIG. 1C is a graph depicting rates of relaxation in wild type and TRPV2 knockout mice.

Using the intact anesthetized mouse model, the cardiac and vascular effects of increasing doses of probenecid were examined by measuring LV pressure development and carotid artery blood flow, simultaneously. As shown in FIGS. 1A and 1B, cardiac contractile performance was significantly lower in TRPV2$^{-/-}$ mice compared to WT, at both baseline and during infusion of probenecid. Invasive measurements of cardiac function demonstrate that TRPV2 abrogration (TRPV2-/-) has decreased systolic function at baseline as evidenced by (FIG. 1A) decreased maximum developed pressure/time (dP/dt$_{max}$) and (FIG. 1B) at 40 mmHg of developed pressure (dP/dt$_{40}$) with a trend towards decreased diastolic function as noted with (FIG. 1C) negative developed pressure/time (dP/dt$_{min}$). Importantly, administration of probenecid resulted in a robust stimulation of contractile function in WT mice, and this effect was markedly attenuated in the TRPV2$^/$ mice. The observed effects of probenecid on LV dP/dt were generally maximal within one minute of bolus administration, and were stable for at least 5 minutes (at the time of reported measurement). A similar pattern of responses was observed for dP/dt min, as an index for diastolic function (FIG. 1C).

Ex Vivo Function in Vascular Smooth Muscle.

Ex vivo function in vascular smooth muscle was examined. Initial studies in isolated aortae were performed to examine whether there were any vasoconstrictor effects of probenecid over the relevant concentration range, and no evidence was found of increased force production, with or without intact endothelium, even at concentrations as high 10 mM (data not shown). Next, the relaxing effects of increasing concentrations of probenecid was examined after pre-contracting the vessels segments with 3 mM phenylephrine, and results are shown in FIGS. 2A-2D. In endothelium-denuded vessels (–E, FIGS. 2A and 2B), there were no differences in maximal developed tension in response to phenylephrine between wild type (n=8) and TRPV2$^{-/-}$ (n=8) mice (5.99±0.74 vs 6.07±0.55 mN). In response to increasing concentrations of probenecid in these pre-contracted vessels, there was no significant dilatory response until a concentration of 1 mM, and at 10 mM, developed tension was reduced to about 25% of maximum in both groups of mice (FIG. 2B). There were no differences in the concentration-response characteristics between wild type and TRPV2$^{-/-}$ mice without endothelium (EC$_{50}$: 4.56±0.34 vs 4.59±0.52 mM respectively).

In wild type and TRPV2$^{-/-}$ vessels with intact endothelium (+E, FIGS. 2C and 2D), maximal developed tension in response to phenylephrine was substantially less than in –E vessels, but was not different between the two genotypes (1.45±0.12 vs 1.75±0.25 mN in WT and TRPV2$^{-/-}$, respectively). Vessels with intact endothelium were somewhat more sensitive to probenecid than –E vessels, but again there were no differences in the concentration-response characteristics between the two genotypes (EC$_{50}$: 0.67±0.21 vs 0.52±0.11 mM respectively, FIG. 2D). The increased responsiveness of +E vessels to probenecid suggests some participation of the endothelium in the dilatory response to probenecid, but through a TRPV2-independent mechanism Isolated Cardiomyocyte Function.

In order to further examine the mechanisms associated with decreased contractility in TRPV2$_{-/-}$ mice in vivo, we evaluated the mechanical properties in isolated cardiomyocytes, representing a load-independent system. Compared to WT, TRPV2$_{-/-}$ myocytes had significantly reduced fractional shortening (FS, P<0.001, FIG. 3A), shortening rate (+dL/dt, P<0.001, FIG. 3B) and relengthening rate (–dL/dt, P<0.001, FIG. 3C). FIG. 3D is a representative tracing of cell lengths in the wild type (WT) and knockout (KO) mice.

Discussion

Regarding the mechanism of action of TRPV2, probenecid therapy had previously been shown, putatively through TRPV2 stimulation, to result in increases cytosolic Ca$^{2+}$ concentrations and increased Ca$^{2+}$ sparks in isolated WT cardiomyocytes. It was also previously demonstrated that TRPV2 overexpression, previously known as growth factor-regulated channel (GRC), in the heart results in cardiomyopathy due to Ca$^{2+}$ overloading. This finding was extrapolated by investigators to suggest that TRPV2 is a "key player" in the myocyte degeneration even though total cell receptor concentration is not different between normal and dystrophic muscles. Hence, it can be argued that under physiologic conditions TRPV2 plays a minor, though clinically relevant and easily measurable role in myocyte relaxation through minor changes in Ca$^{2+}$ transients, though under experimental conditions of marked overexpression the influx of Ca$^{2+}$ is significantly higher and hence associated with the development of cardiomyopathy.

Regarding the role that TRPV2 plays in the vascular tone, no vascular phenotype is associated with TRPV2 abrogation and at low and high doses, there is no significant vasoactive effect of probenecid (even in deendothelialized vessels). This important finding has significant implications for the treatment of HFpEF in humans, as a safe and positive lusitrope that has a neutral effect on blood pressure can be a potential first therapy for these patients.

Probenecid, an FDA approved drug with a very safe clinical profile, also had inotropic properties that for decades had been overlooked. This effect is secondary to transient increases in cytosolic Ca$^{2+}$ through sarcoplasmic reticulum (SR) release and not through the traditional inotropic pathway of β-ADR stimulation. All currently available positive inotropes used clinically either stimulate β receptors directly, or downstream (i.e, milrinone) and have been found to increase metabolic demand, activate pro-apoptotic signaling pathways and promote malignant arrhythmias that result in increased mortality. Furthermore, all but one of these inotropes also stimulate vascular adrenergic receptors resulting in vasoconstriction and increased afterload which limit their clinical usefulness. The data herein not only confirm previous findings that probenecid is an inotrope as determined with invasive measurements, but also describe for the first time that low (30 mg/kg) and high (100 mg/kg) probenecid doses results in increased lusitropy in WT mice.

CONCLUSION

TRPV2 may contribute to the SR novel property of probenecid functioning as a positive lusitrope with neutral vascular effects. These data suggest that TRPV2 agonists can provide therapeutic options for patients with diastolic cardiac dysfunctions such as HfpEF and its precursor conditions.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the general inventive concept.

What is claimed is:

1. A method of treating heart failure with preserved ejection fraction (HFpEF) in a subject comprising intravenously infusing an amount of probenecid to achieve a plasma concentration effective to treat the cardiac dysfunction heart failure with preserved ejection fraction in the subject.

2. The method of claim 1 wherein the amount of probenecid is sufficient to result in an improved performance on a standardized 6 minute walk test, an improved New York Heart Association (NYHA) classification, a lower diuretic dose requirement, a lower serum B-type Natriuretic Peptide (BNP) level, a normalization of serum sodium concentration, or combinations thereof.

3. The method of claim 1 using a bolus injection or continuous intravenous infusion.

4. The method of claim 1 wherein a dose of probenecid ranges from about 1 mg/kg/day to about 100 mg/kg/day.

5. The method of claim 1 wherein probenecid is administered over a period of about 24 hours per day.

6. The method of claim 1 wherein the subject is treated with probenecid for at least one week.

7. The method of claim 1 wherein the subject is treated with probenecid for at least one month.

8. A method of treating heart failure with preserved ejection fraction in a subject comprising administering probenecid to the subject in a dosing regimen to maintain a therapeutic plasma concentration to treat the heart failure with preserved ejection fraction in the subject.

9. The method of claim 8 wherein the therapeutic plasma concentration of probenecid is sufficient to result in an improved performance on a standardized 6 minute walk test, an improved NYHA classification, a lower diuretic dose requirement, a lower serum BNP level, a normalization of serum sodium concentrations, or combinations thereof.

10. The method of claim 8 wherein the dosing regimen includes intravenous administration of the dose of probenecid.

11. The method of claim 8 wherein probenecid is administered for at least one week.

12. The method of claim 1 where treating HFpEF includes curing the patient.

* * * * *